United States Patent
Mertelmeier et al.

(10) Patent No.: US 9,282,942 B2
(45) Date of Patent: Mar. 15, 2016

(54) DEVICE AND METHOD FOR A DIAGNOSTIC APPARATUS

(71) Applicants: Thomas Mertelmeier, Erlangen (DE); Ralf Nanke, Neunkirchen am Brand (DE)

(72) Inventors: Thomas Mertelmeier, Erlangen (DE); Ralf Nanke, Neunkirchen am Brand (DE)

(73) Assignee: Siemens Aktiengesellschaft, Munich (DE)

(*) Notice: Subject to any disclaimer, the term of this patent is extended or adjusted under 35 U.S.C. 154(b) by 35 days.

(21) Appl. No.: 13/939,393

(22) Filed: Jul. 11, 2013

(65) Prior Publication Data

US 2014/0016741 A1 Jan. 16, 2014

(30) Foreign Application Priority Data

Jul. 11, 2012 (DE) .......................... 10 2012 212 136

(51) Int. Cl.
*A61B 6/00* (2006.01)
*A61B 6/04* (2006.01)
*A61B 6/02* (2006.01)

(52) U.S. Cl.
CPC ............... *A61B 6/502* (2013.01); *A61B 6/0414* (2013.01); *A61B 6/025* (2013.01)

(58) Field of Classification Search
CPC ....... A61B 6/502; A61B 6/0414; A61B 6/025

USPC ............................................................. 378/37
See application file for complete search history.

(56) References Cited

U.S. PATENT DOCUMENTS

| | | | |
|---|---|---|---|
| 4,943,986 A * | 7/1990 | Barbarisi | 378/37 |
| 6,480,565 B1 | 11/2002 | Ning | |
| 6,999,554 B2 * | 2/2006 | Mertelmeier | 378/37 |
| 8,787,522 B2 * | 7/2014 | Smith | A61B 6/025 378/20 |
| 2005/0100129 A1 | 5/2005 | McKenna | |
| 2005/0113681 A1 * | 5/2005 | DeFreitas et al. | 600/426 |
| 2005/0129172 A1 * | 6/2005 | Mertelmeier | A61B 6/502 378/37 |
| 2009/0103796 A1 * | 4/2009 | Akagi et al. | 382/132 |
| 2010/0067648 A1 * | 3/2010 | Kojima | 378/11 |
| 2011/0129062 A1 | 6/2011 | Hoernig | |

FOREIGN PATENT DOCUMENTS

EP 0 370 089 B1 3/1994

* cited by examiner

*Primary Examiner* — David J Makiya
*Assistant Examiner* — Dani Fox
(74) *Attorney, Agent, or Firm* — Schiff Hardin LLP

(57) ABSTRACT

In this device and the associated method, a connection unit that can be attached to an arm bearing an x-ray source and an x-ray receiver is fashioned such that said connection unit compensates for a pivot movement of the arm so that a compression unit arranged at the connection unit remains stationary during a pivot movement.

12 Claims, 4 Drawing Sheets

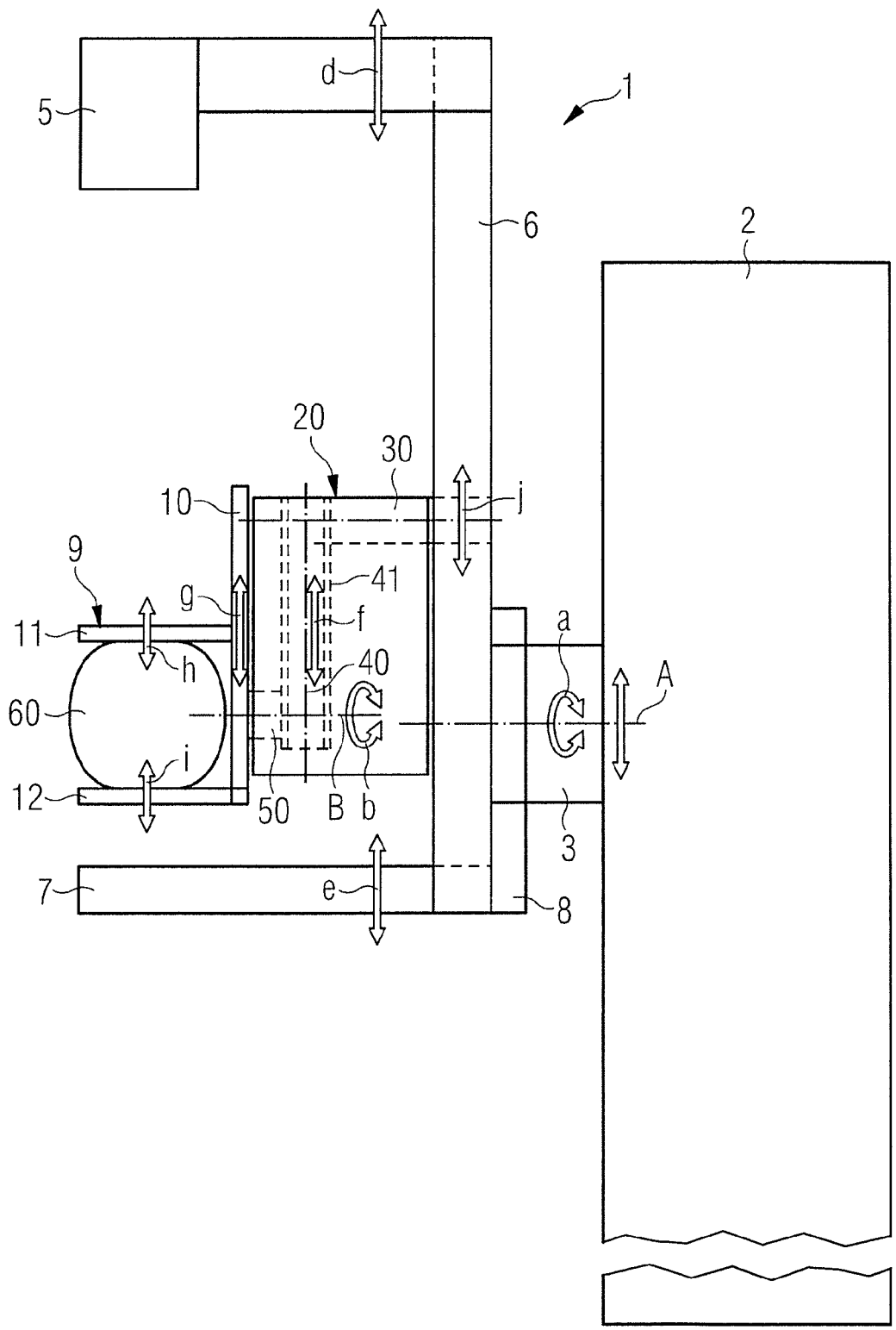

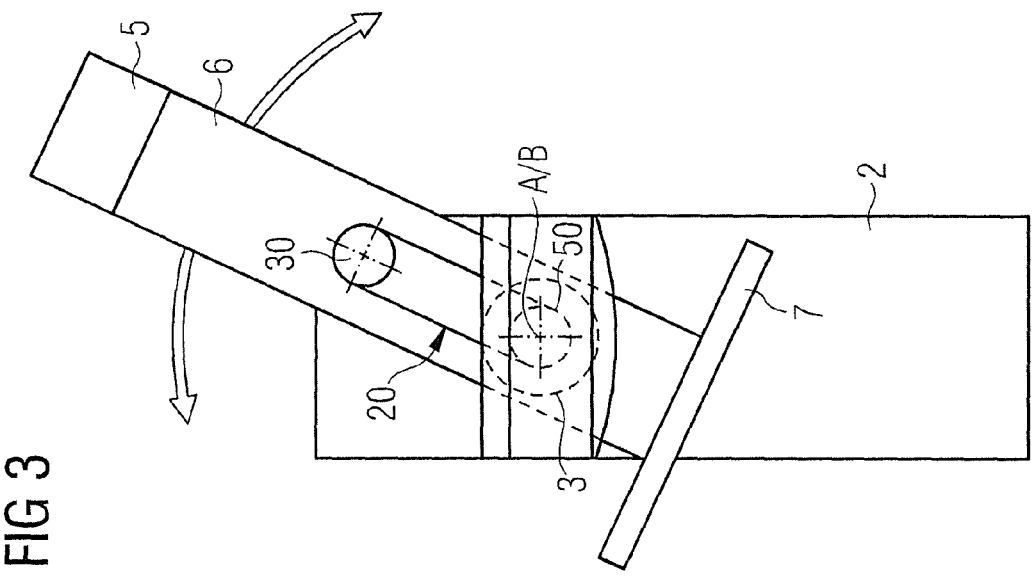
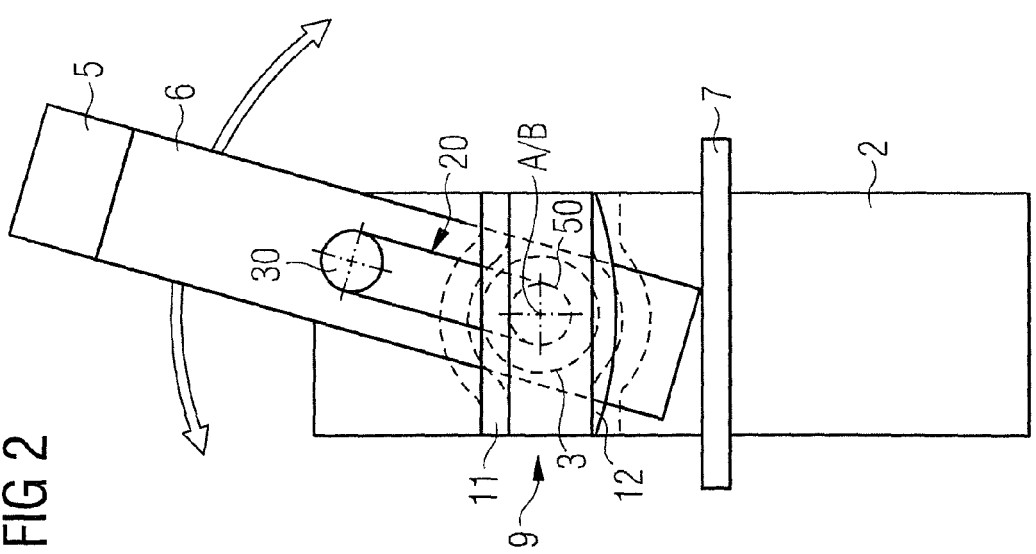

DEVICE AND METHOD FOR A DIAGNOSTIC APPARATUS

BACKGROUND OF THE INVENTION

1. Field of the Invention

The invention concerns a device and method for a diagnostic apparatus.

2. Description of the Prior Art

A diagnostic apparatus (in particular an x-ray diagnostic apparatus for mammography) with a compression unit is described in EP 0 370 089 B1, for example. The x-ray diagnostic apparatus has a support arm that can be pivoted around a horizontally traveling axle. A compression device for a breast is arranged on the support arm. Furthermore, a frame part is connected with the support arm. An x-ray source and an x-ray receiver are arranged opposite one another on the frame part. The frame part can be adjusted in straight lines in guides, relative to the support arm and to the compression device. The horizontally traveling axle is arranged relative to the compression device so that this is essentially aligned with the breast axis of a compressed breast. By the common pivoting of the x-ray source, the x-ray receiver and the compression device around the horizontally proceeding axle, this x-ray diagnostic apparatus allows an examination method to be executed in which x-ray exposures of a compressed breast are acquired without the patient needing to vary her location. A disadvantage of this known x-ray diagnostic apparatus is that the breast must be repositioned and compressed for each x-ray image in an acquisition cycle.

SUMMARY OF THE INVENTION

An object of the invention is to provide an improvement of such a diagnostic apparatus.

In the device and the associated method in accordance with the invention, an arm with a compression unit arranged between an x-ray source and an x-ray receiver is fashioned on a pivotable support arm, such that the compression unit with a controllable connection unit is connected with the arm. The controllable connection unit can compensate for rotation movements of the arm.

The invention has the advantage that a number of 2D x-ray exposures can be made with a single fixing of the breast.

The invention also has the advantage that the central beam of the x-ray source is aligned orthogonally to the detector so that a uniform exposure of the detector results for 2D projections from different angles, as occur in the acquisition images in tomosynthesis.

The invention also has the advantage that a common movement of the x-ray source and the x-ray receiver is enabled along orbits around a common rotation point in cone beam geometry.

BRIEF DESCRIPTION OF THE DRAWINGS

FIG. 1 schematically illustrates an x-ray diagnostic apparatus in accordance with the invention.

FIGS. 2 through 5 show different front views of the x-ray diagnostic apparatus.

DESCRIPTION OF THE PREFERRED EMBODIMENTS

Figure 5:
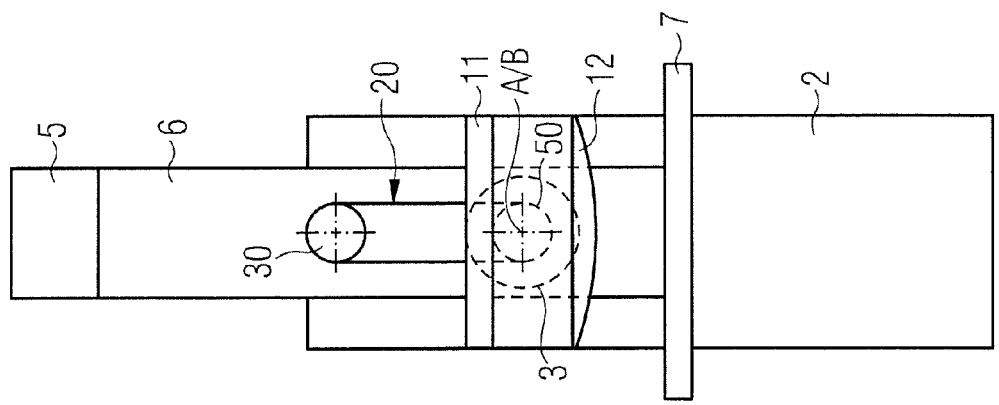

In the device and the associated method in accordance with the invention, a connection unit that can be attached to an arm bearing an x-ray source and an x-ray receiver is fashioned such that the connection unit compensates for a pivot movement of the arm, so that the compression unit arranged at the connection unit remains stationary during a pivot movement of the arm.

In the present exemplary embodiment, the x-ray diagnostic apparatus 1 for mammography examinations that is shown in FIG. 1 has a stand 2 provided with a support arm 3. A horizontally extending first rotation axle A is indicated in the support arm 3. The rotation directions of the first axle A are indicated with double arrow a. The mounting of the support arm 3 in the stand 2 is vertically adjustable in a guide. The vertical adjustment of the support arm 3 can take place manually, with motor assistance, or purely in a motorized manner (these being known but not shown). An arm 6 provided with an x-ray source 5 and an x-ray receiver 7 is arranged on the support arm 3. The x-ray receiver 7 can be, for example, an x-ray film, an x-ray image intensifier or a flat panel detector. A compression unit 9 is arranged on the arm 6, between the x-ray source 5 and the x-ray receiver 7. The compression unit 9 is connected with the arm 6 via a connection unit 20. The connection unit 20 enables an independent alignment of the compression unit 9 relative to the angle of the arm 6. The connection unit 20 enables a separation of the compression unit 9 from the arm 6.

In one embodiment, the connection unit 20 has a number of sub-elements 30, 40, 41, 50. As shown with FIG. 1, for example, these sub-elements are a first sub-element 30, a second sub-element 40, 41 and a third sub-element 50. The first and third sub-elements 30, 50 can be arranged aligned horizontally. A second rotation axle B runs through the third connection element. This second rotation axle B lies parallel to the first rotation axle A. The second sub-elements 40, 41 are arranged between the first and third sub-elements 30, 50. The second sub-elements 40, 41 are variably adjustable in terms of its length. The length change can take place manually, semi-manually or in a motorized manner. A height adjustment of the compression unit 9 can be achieved with a length change of the second sub-elements 40, 41. If a length adjustment of the second sub-elements 40, 41 is not present, a height adjustment of the compression unit 9 can be produced by the detachable third connection element 50 at a rear wall accommodating an upper and lower compression plate, or upper and lower compression units 11, 12. A height adjustment of the compression unit 9 can likewise take place by a height-adjustment insert for the first sub-element 30 at the arm 6.

The first and third sub-elements 30, 50 can each have a motor-controllable coupling unit compensating for a rotation of the first rotation axle, wherein these can be controlled together or individually. The compression device 9 (which has the upper and lower x-ray-transparent compression elements 11, 12) can be adjusted or used corresponding to the examination requirements. The entire compression device 9 or individual compression plates 11, 12 can also be removed according to the examination requirements.

The shape of the compression plates can be biplanar or plano-convex. Likewise, for a 360° scan the upper and lower compression plate can each have the shape of a half-cylinder with a possibility to form a negative pressure, for example.

The x-ray-transparent compression elements 11, 12 that can be detachably affixed to the front side of a rear wall 10 can be displaced in height along at least one guide rail. If a longitudinal adjustment of the second sub-elements 40, 41 is not present, a height adjustment of the compression unit 9 can also be produced by a detachable connection element between a rear wall 10 accommodating the upper and lower compression elements 11, 12. For this the detachable connection element is directed along a guide rail traveling vertically, for example.

The compression unit 9 can be pivoted together with the arm 6 around the first rotation axle A. A pivoting of the compression unit 9 around the first rotation axle A is subsequently described in exemplary embodiments. The detachable connection unit 20 between the compression unit 9 and the arm 6 enables an exchange of the compression unit 9 for another compression unit 9 which is better suited to an examination case. In an exchange, either the connection unit 20 with the compression unit 9, or just the compression unit 9, can be exchanged. A faster exchange of the compression unit 9 is made possible by means of a detachable connection to the arm 6 of the connection unit 20. A breast 60 compressed with the compression unit 9 is schematically presented in FIG. 1. The compression unit 9 and the connection unit 20 can be arranged on the arm 6 such that the first rotation axle A of the support arm 3 aligns with the breast axis of a breast 60.

In the exemplary embodiment, both the arm 6 provided with the x-ray source 5, and the mount 8 connected with the x-ray receiver 7, can be pivoted around the first rotation axle A of the support arm 3. The arm 6 is accordingly pivotable around the support arm 3, and around the first rotation axle A relative to the mount 8 and the compression unit 9. In the exemplary embodiment, the pivot movements of the arm 6 and the mount 8 take place in a motorized manner. Electric motors are provided for this at the x-ray diagnostic apparatus. The activation of the motors takes place via a control device (associated with a computer) based on inputs made at a control panel (not shown). In addition, in the exemplary embodiment the x-ray source 5 is adjustable along the arm 5 corresponding to the drawn double arrow d, and the x-ray receiver 7 is adjustable along the mount 8 (see double arrow e) in the direction of the support arm 3. The x-ray receiver 7 can also be arranged so as to be movable directly at the arm 6. For example, the adjustment takes place in a straight line in guide rails that are not explicitly shown in the figures. The adjustment takes place in a motorized manner, controlled by a control device (not shown). The electric motors required for this are not explicitly shown in the figures. The adjustment can also take place manually in connection with an arrestable latching unit. With the movement directions d, e, f, g, h, i and j of sub-components that are shown in FIG. 1, optimal adjustments can be made for a patient and for the x-ray exposures.

Front views of different use forms of an x-ray diagnostic apparatus for various acquisition possibilities are illustrated in FIGS. 2 through 5.

According to a variant of the invention, via the connection unit 20 the compression unit 9 can be coupled with the arm 6 (which has an x-ray source 5 and an x-ray receiver 7) such that this can be rotated together with said arm 6. The position of the compression elements 11, 12 of the compression unit 9 remains static. In this way it is ensured that x-ray source and x-ray detector move around the compressed breast while 2D projections of a compressed breast 60 are acquired and, at the same time or with time offset, the digitally present x-ray image data are calculated into volume data. For example, the respective active connections between the connection unit 20 and the compression unit 9 can be a mechanical coupling or an electronically controlled alignment of the first, second and/or third sub-elements 50, 40, 41, 30 of the connection unit 20.

In FIG. 2, an operating mode is presented in which the upper and lower compression elements 11, 12 of the compression unit 9 and the x-ray receiver 7 are kept stationary, and only the arm 6 provided with the x-ray source 5 is pivoted by means of an electric motor around the horizontally traveling first rotation axle A. The connection unit 20 arranged between the arm 6 and the compression unit 9 counteracts the movement of the arm 6 or, respectively, the rotation of the first rotation axle A, for example with the third sub-element 50. The pivoting of the arm 6 (provided with the x-ray source 5) relative to the x-ray receiver 7 and the compression unit 9 is, for example, useful for a stereotactic biopsy since—in this case given a stationary examination subject (namely the breast 60 that is not shown in FIG. 2)—spatial information of tissue of interest can be acquired from x-ray exposures of the breast from different angles in order to implement an extraction of the tissue. The presentation of the acquired x-ray exposures on a viewing device (not shown) and the determination of the spatial information are determined with the use of a computer associated with the x-ray diagnostic apparatus. Possible different shapes (as already stated above) of the upper and/or lower compression plates 11, 12 are additionally shown in FIG. 2.

An additional operating mode of the x-ray diagnostic apparatus is shown in FIG. 3, in which the arm 6 provided with the x-ray source 5 and the mount 8 provided with the x-ray receiver 7 are moved together around the first rotation axle A, and the upper and lower compression plate 11, 12 remain stationary. For the compression unit 9 to remain stationary, this is moved synchronously around the second rotation axle B, counter to the rotation direction of the first axle A. The first and second rotation axles A, B rest on one another. For example, the third sub-element 50 of the connection element 20 implements a counter-rotation movement synchronously with the pivot movement of the arm 6, such that the upper and lower compression elements 11, 12 remain stationary while the x-ray source 5 travels along an circular arc segment or circular arc. The alignment of the x-ray source 5 with the x-ray receiver 7 is retained in such a manner that a central beam emanating from the x-ray source 5 strikes orthogonally on the receiver surface of the x-ray receiver 7. In the exemplary embodiment, the compression unit 9 remains stationary at its starting location. The operating mode of the x-ray diagnostic apparatus that is shown in FIG. 3 is suitable for tomosynthesis. In this operating mode, the x-ray source 5 and the x-ray receiver 7 move around the subject 60 arranged stationary in space, wherein 2D projections of the subject 60 are acquired from different directions in order to reconstruct a volume data set as well as slice images from these with the use of a computer (not depicted here). In this embodiment shown for tomosynthesis, the coupled movement of x-ray source 5 and x-ray receiver 7 results in a larger field of view than given a stationary x-ray receiver 7.

Figure 4:
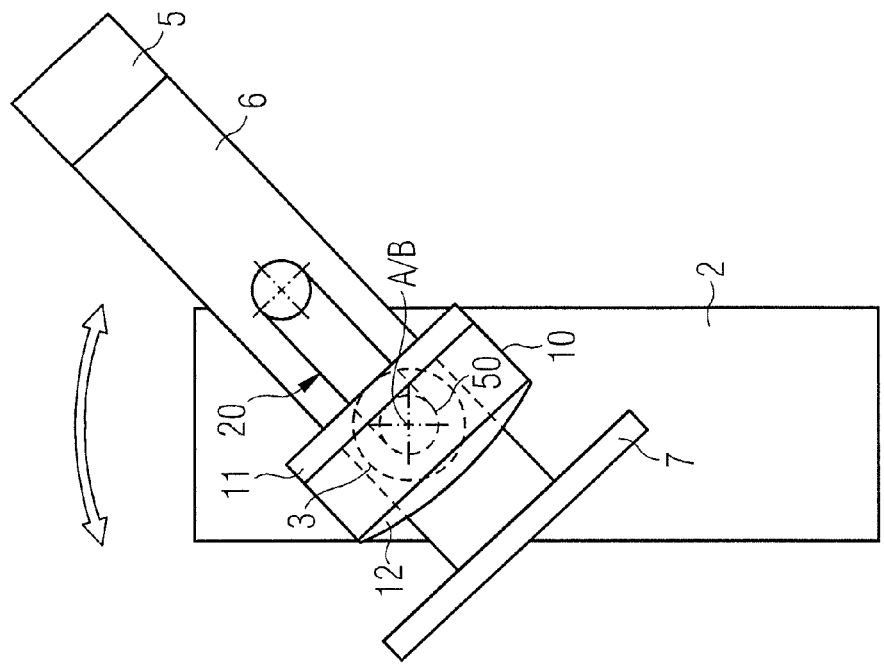

Additional operating modes of the compression device 9 are illustrated in FIGS. 4 and 5, in connection with the x-ray diagnostic apparatus. In these operating modes, only the support arm 3 is pivoted around the horizontally traveling first rotation axis A with the aid of the electric motor, while the alignment of the x-ray source 5, the x-ray receiver 7 and the compression unit 9 relative to one another is thereby maintained. This operating mode is suitable for medio-lateral oblique and lateral x-ray acquisitions of the breast compressed with the compression device 9.

Figure 6:
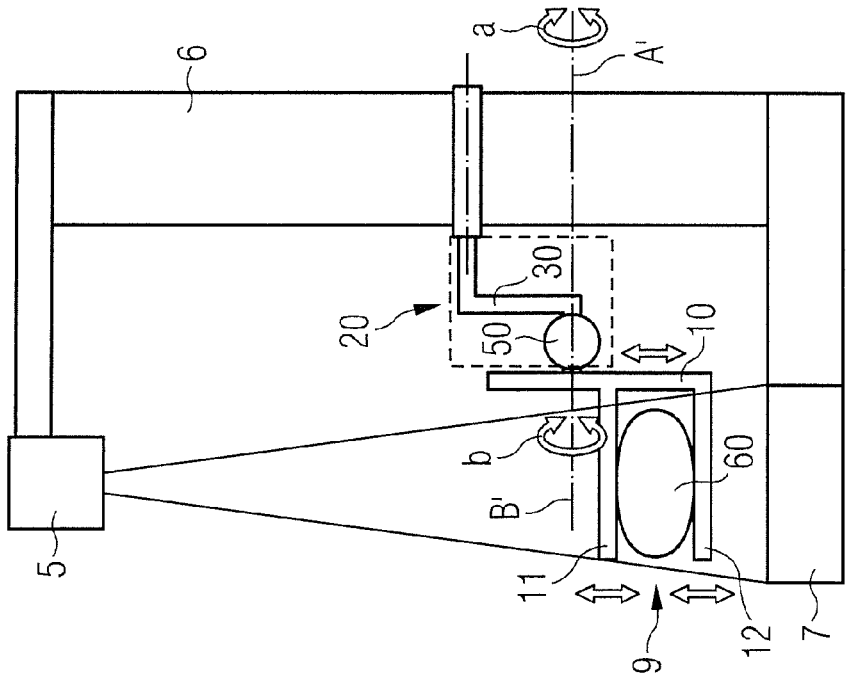
FIG. 6 is a side view of the x-ray diagnostic apparatus of FIG. 1.

In a further embodiment of the connection unit 20 in connection with a compression unit 9, a side view of the arm 6 is shown with FIG. 6. The first and second rotation axles A and B are indicated with the respectively indicated possible rotation directions a, b. The connection unit 20 shown here can be formed from the first sub-element 30 and the third sub-element 50. The first sub-element 30 is connected at a first end with the arm 6 and at a second end with the third sub-element 50. In this embodiment, the third sub-element 50 is fashioned with a motorized controllable coupling (for example a friction clutch). The third sub-element 50 is connected at a first with the second end of the first sub-element 30. The second end of the third sub-element 50 is connected with the back side of the rear wall 10 guiding the upper and lower compression plates 11, 12. The third connection element 50 can be designed such that this is engaged in an active connection with a guide rail arranged at the back side of the rear wall. In addition to a separation capability of the compression unit 9 from the connection element 20, this brings with it the advantage that the height of the compression unit 9 is variably adjustable relative to the patient.

The exemplary embodiments described in the preceding are to be understood as examples. For example, the pivot movements of the support arm 3, the adjustments at the arm 6 and the control of the mount 8 are not necessarily positioned or, respectively, moved by a motor, but rather can be positioned or, respectively, moved manually or assisted by a motorized drive. The motor for the mount 8 can also be omitted entirely if (for example) a mechanical coupling is present between the arm 6 and the mount 8 in order to rotate the arm 6 and the mount 8 together around the first rotation axle A.

Figure 7:
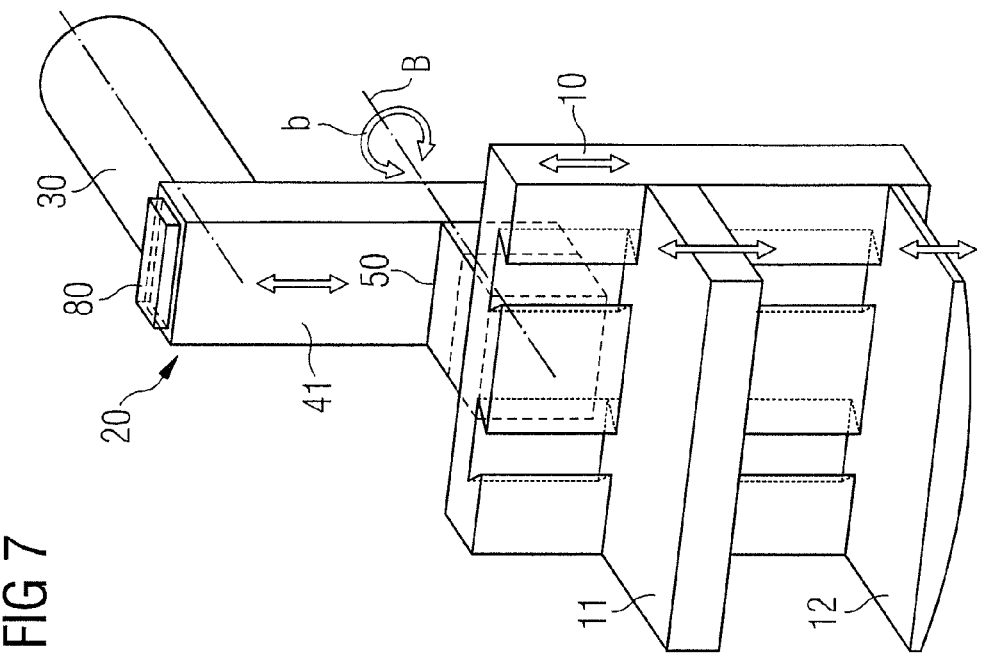
FIG. 7 is a perspective view of a compression unit with a connection unit that are suitable for use in the x-ray diagnostic apparatus of FIG. 1.

The compression unit 9 is depicted with the connection unit 20 in FIG. 7. In this embodiment, the compression unit 9 is formed from an upper and lower compression plates 11, 12 and from a rear wall 10 accommodating the two plates. The upper and lower compression plates 11, 12 are fashioned such that these are positionable independently of one another along at least one guide groove. The upper and lower compression plates 11, 12 can be removed from the guide groove. The lower compression plate 12 is rounded on its underside. The upper and/or lower compression plate 11, 12 can also be fashioned in the shape of a semi-arc. In a further variant, the upper and lower compensation plates 11, 12 can each be curved in the shape of a semicircle. The compression unit 9 can also be formed as a cylinder, wherein the possibility exists to generate a negative pressure in the cylinder. As indicated above, the upper and lower compression plates 11, 12 are connected via the rear wall 10. The rear wall is connected with the connection unit 20 so as to be detachable. The detachable or arrestable connection elements between the rear wall 10 and parts of the connection unit 20 can likewise be partially directed in a guide unit. With the detachable or arrestable connection elements, the compression unit 9 can be shifted upward relative to a patient standing in front of said compression unit 9. A counter-rotation can take place synchronously with the rotation of the support arm 6, controlled by a compression unit (not explicitly shown). In a further embodiment, tilt sensors can be arranged in the connection unit 20. An adjustment of the compression elements of the compression unit that are to be kept horizontal can take place from the control signals emitted by the tilt sensors integrated into the compression elements, for example. For example, if a number of 2D x-ray acquisitions should be applied for a tomosynthesis in a medio-lateral oblique and lateral positioning of the fixed breast, the inclination of the compression plates 11, 12 can be adjusted by specifying an angle of inclination.

In an embodiment of the invention, the diagnostic apparatus has a control device to control the pivot movements of the support arm 3, the arm 6, the mount 8 and the connection unit 20. The diagnostic apparatus to control the common pivoting of the arm 6 and the mount 8 relative to the compression unit 9 has an image computer for the image reconstruction given tomosynthesis.

In variants of the invention, the x-ray source 5 at the arm 6 can be adjustably arranged along the arm 6 and/or the x-ray receiver 7 at the mount 8 can be adjustably arranged along the mount 8, relative to the compression unit 9. In this way, the possibility exists to implement enlarged x-ray acquisitions of a compressed breast.

Although modifications and changes may be suggested by those skilled in the art, it is the intention of the inventor to embody within the patent warranted hereon all changes and modifications as reasonably and properly come within the scope of his contribution to the art.

We claim as our invention:

1. A mammography apparatus comprising:
    an examination unit comprising a mounting arm connected to a rotatable support arm that rotates said mounting arm, and thereby rotates said examination unit;
    said examination unit comprising an x-ray source mounted to said mounting arm that emits x-rays, a compression unit configured to compress and hold a breast in a path of said x-rays, and an x-ray detector mounted to said mounting arm to detect x-rays attenuated by the breast in the compression unit;
    a connection unit that connects said compression unit to said mounting arm, said connection unit being configured to rotate said compression unit independently of an angle to which said mounting arm is rotated by said support arm; and
    said support arm having a rotational axis around which support arm rotates in order to rotate said examination unit via said mounting arm, and wherein said connection unit comprises an axle connected to said mounting arm that independently rotates said compression unit, said axle having a rotational axis that is parallel to and does not coincide with the rotational axis of said support arm.

2. A mammography apparatus as claimed in claim 1 wherein said connection unit is configured to execute a rotation movement that compensates for a rotation movement imparted to said examination unit, via said mounting arm, by said support arm.

3. A mammography apparatus as claimed in claim 1 wherein said connection unit is detachable from said mounting arm.

4. A mammography apparatus as claimed in claim 1 wherein said connection unit is detachable from said compression unit.

5. A mammography apparatus as claimed in claim 1 wherein said connection unit is detachable from said mounting arm and from said compression unit.

6. A mammography apparatus as claimed in claim 1 wherein said connection unit comprises a sub-element thereof that connects said compression unit with said mounting arm.

7. A mammography apparatus as claimed in claim 1 wherein said sub-element comprises a detachable coupling.

8. A mammography apparatus as claimed in claim 1 comprising an electronically controllable servomotor that operates said connection unit to produce said independent alignment of said connection unit with respect to the rotation angle of said examination unit.

9. A mammography apparatus as claimed in claim 1 wherein said connection unit comprises a sub-element connected to said compression unit that allows height adjustment of said compression unit.

10. A mammography apparatus as claimed in claim 1 wherein said compression unit comprises an upper compression element and a lower compression element and wherein at least one of said upper compression element and said lower compression element is adjustable in height.

11. A mammography method comprising:
   placing a female breast in a compression unit and compressing and holding the breast in said compression unit;
   irradiating the breast with x-rays from an x-ray source mounted to a mounting arm, to which an x-ray detector is also mounted, and detecting x-rays attenuated by the compressed breast in the compression unit with said x-ray detector while rotating said mounting arm around a first rotational axis;
   connecting said compression unit to said mounting arm via a connection unit that has an axle that rotates the compression unit relative to the mounting arm around a second rotational axis that is parallel to and does not coincide with said first rotational axis; and
   rotating the compression unit around said second rotational axis independently of an angle to which the mounting arm is rotated around said first rotational axis.

12. A mammography method as claimed in claim 11 comprising, with said connection unit, executing a rotation movement that compensates for a rotation movement imparted to said mounting arm.

* * * * *